United States Patent [19]
Ottlinger et al.

[11] Patent Number: 5,759,366
[45] Date of Patent: Jun. 2, 1998

[54] $CO_2$ SENSOR AND MEASUREMENT CIRCUIT USING THE SENSOR

[75] Inventors: Marion Ottlinger; Adalbert Feltz, both of Deutschlandsberg, Austria

[73] Assignee: Siemens Matsushita Components GmbH & Co. KG, Munich, Germany

[21] Appl. No.: 679,981

[22] Filed: Jul. 15, 1996

[30] Foreign Application Priority Data

Jul. 14, 1995 [DE] Germany ............... 195 25 764.2

[51] Int. Cl.⁶ .................................................. G01N 27/407
[52] U.S. Cl. ........................... 204/424; 204/402; 204/421; 204/426; 205/687; 205/784
[58] Field of Search .................... 204/421–429, 204/402; 205/784, 784.5, 785, 687

[56] References Cited

U.S. PATENT DOCUMENTS

| | | |
|---|---|---|
| 4,298,573 | 11/1981 | Fujishiro .......................... 204/425 |
| 5,194,134 | 3/1993 | Futata et al. ..................... 204/427 |

FOREIGN PATENT DOCUMENTS

| | | |
|---|---|---|
| 0 468 249 A1 | 1/1992 | European Pat. Off. . |
| 42 25 624 A1 | 2/1994 | Germany . |
| 94/28403 | 12/1994 | WIPO . |

OTHER PUBLICATIONS

Ionic conductivity of NASICON–type conductors $Na_{1.5}M_{0.5}Zr_{1.5}(PO_4)_3$ ($M:Al^{3+},Ga^{3+},Cr^{3+},Sc^{3+},Fe^{3+},In^{3+},Yb^{3+},Y^{3+}$), (Saito et al.), 6030 Solid State Ionics, Dec. 1992, No. 3/4, Amsterdam, NE, pp. 327–331.

"High–performance solid–elctrolyte carbon dioxide sensor with a binary carbonate electrode", Miura et al.), 8253b Sensors and Actuators B Chemical, Oct. 1992, No. 3, Lausanne, CH, pp. 165–176.

"Carbon Dioxide Sensor Using Sodium Ion Conductor and Binary Carbonate Auxiliary Electrode", (Miura et al.), dated May 1992, Journal of the Electrochemical Society, vol. 139, No. 5, pp. 1384–1388.

"Potentiometric Gas Sensor for Carbon Dioxide Using Solid Electrolytes", (Maruyama), dated 1987 month unavailable, Solid State Ionics 23, North Holland, pp. 107–112.

"Solid State Electrochmical $CO_2$ Gas Sensor Using Zircon––Based Sodium Ionic Conductors", (Sadaoka et al.), dated 1993 month unavailable, Journal of Materials Science 28, Japan, pp. 2035–2039.

"Solid State Chemical Sensors in Thick Film Technique", (Erdmann et al.), dated Sep. 1990, Micro System Technologies 10–13, Berlin, pp. 1–6.

"Thin and Thick Film Electrochemical $CO_2$ Sensors", (Chu et al.), dated 1992 month unavailable, Solid State Ionics 53–56, North Holland, pp. 80–84.

*Primary Examiner*—T. Tung
*Attorney, Agent, or Firm*—Herbert L. Lerner; Laurence A. Greenberg

[57] ABSTRACT

A $CO_2$ sensor includes a body of solid electrolyte ceramic with alkali ion conductivity, and two electrodes of conductor material being inert with respect to the solid electrolyte ceramic. At least one of the electrodes is at least partially permeable, and the solid electrolyte ceramic is galvanically prepolarized. A measurement circuit configuration includes the $CO_2$ sensor and a voltage measuring device coupled to the electrodes of the solid electrolyte ceramic body.

8 Claims, 3 Drawing Sheets

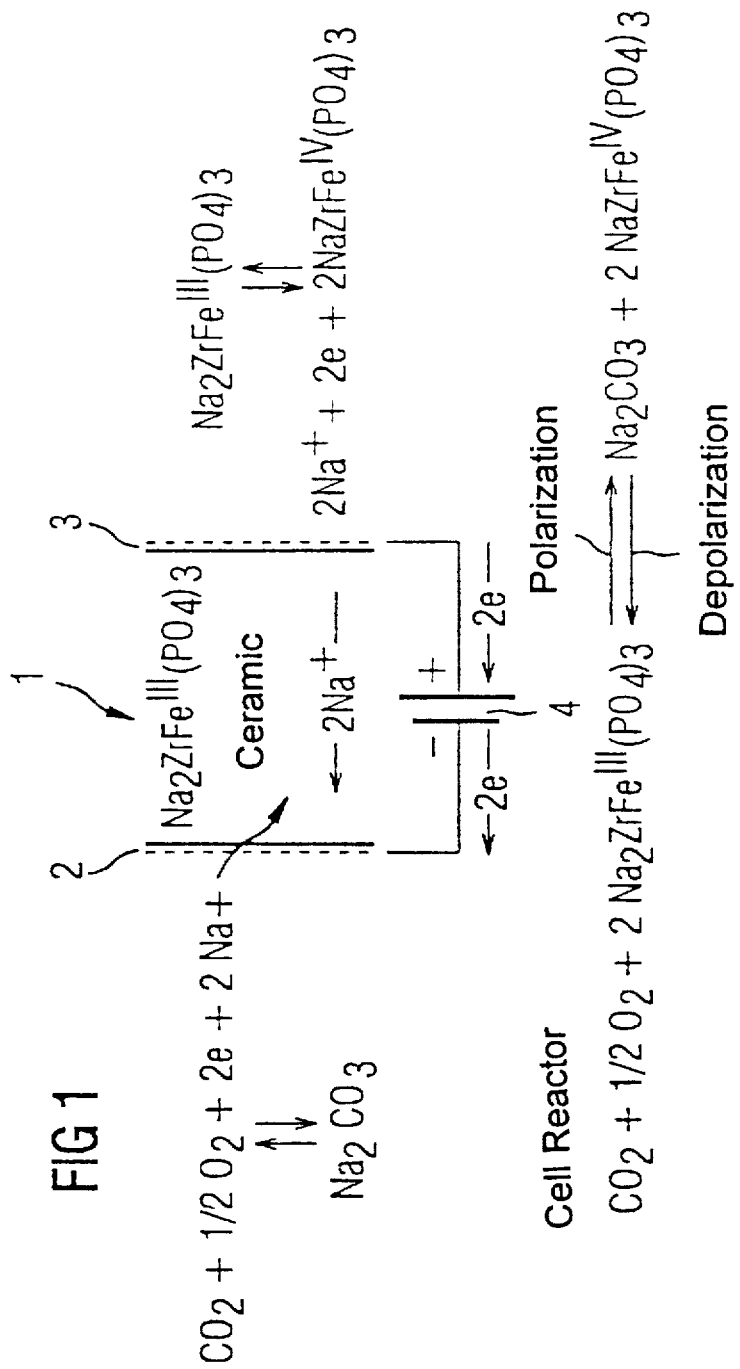

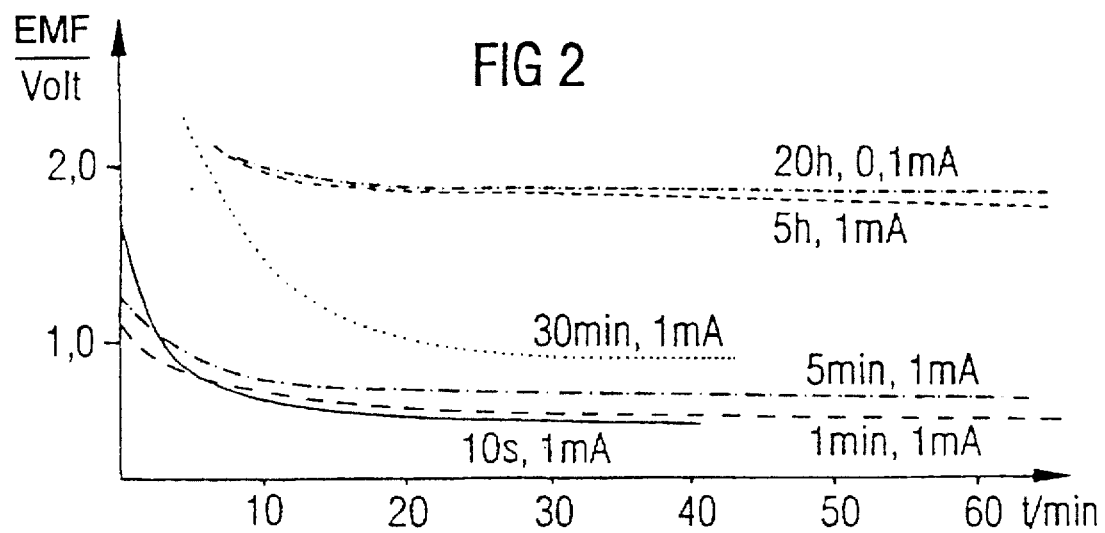
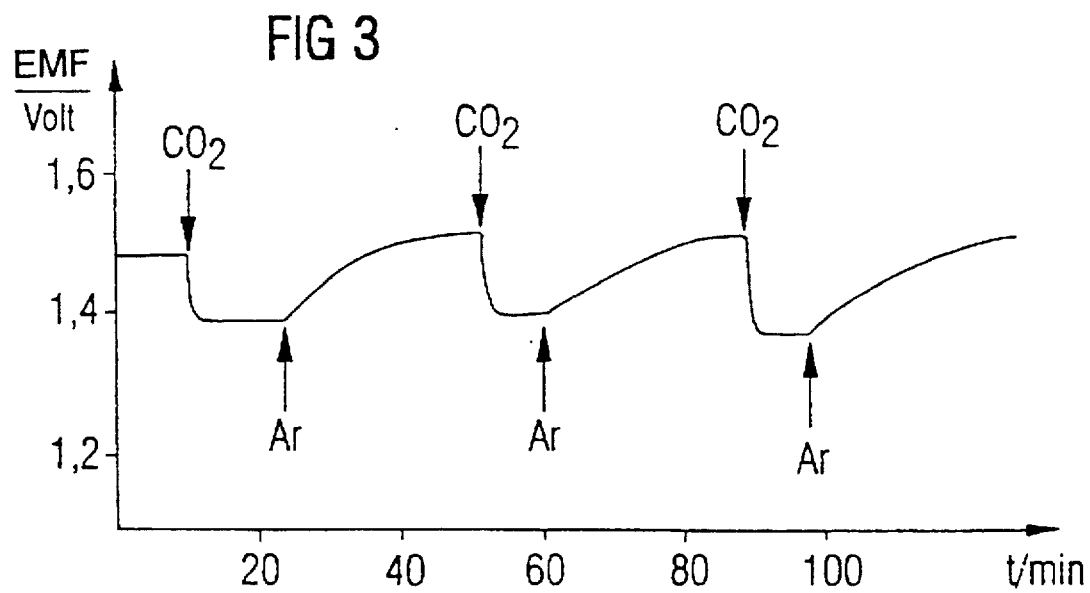

CO₂ SENSOR AND MEASUREMENT CIRCUIT USING THE SENSOR

BACKGROUND OF THE INVENTION

FIELD OF THE INVENTION

The invention relates to a $CO_2$ sensor including a solid electrolyte ceramic body with alkali ion conductivity, having two electrodes of conductor material being inert with respect to the solid electrolyte ceramic. The invention also relates to a measurement circuit configuration using such a sensor.

The sensor is a sensor for determining the $CO_2$ content in gases. Such sensors are of interest for controlling air quality in closed rooms or the composition of the air in greenhouses, in order to ascertain conversion rates of chemical reactions with the involvement of $CO_2$, and in the field of medical diagnostics as well as, for instance, in environmental monitoring to record fluctuations in the $CO_2$ content of the earth's atmosphere.

Electrochemical configurations for measuring the $CO_2$ partial pressure of air or other gas mixtures have been disclosed on the basis of $Na^+$-ion-conducting solid electrolyte ceramics, for instance using β-aluminum oxide or substances of the NASICON system $Na_{1+3x}Zr_2(PO_4)_{3-3x}(SiO_4)_{3x}$, where $0<x<1$.

That is done by coating the surface, which is provided on both sides with a dissipation electrode generally being formed of a noble metal such as platinum, on one side with a layer of a suitable carbonate, such as $Na_2CO_3$. Given an adequately high temperature, the result is a reversible adjustment of a potential-forming equilibrium $Na_2CO_3 <=> 2Na^+ +½O_2+CO_2$, specifically as a result of the transfer of $Na^+$ ions to the solid electrolyte with simultaneous giving up of electrons and liberation of oxygen and $CO_2$. Due to the high mobility of the $Na^+$ ions in the solid electrolytes, the result in the region of the counter electrode in the presence of air with electron acceptance is the formation of $Na_2CO_3$ in fixed solution in the solid electrolyte ceramic. Such a configuration has an electromotive force (EMF) which depends on the $CO_2$ partial pressure of the surroundings and accordingly has a sensor function (see, for instance, Solid State Ionics 23 (1987) pp. 107–112). In addition to discrete sensor elements, miniaturized configurations are also known. They are manufactured by using established technologies, such as thick-film technology, in a way that meets the demands of Microsystems technology (see, for instance, Micro System Technologies, Sep. 10–13, 1990, Berlin, pp. 1–6; Solid State Ionics 53–56 (1992), pp. 80–84; J. Electrochemical Soc. 139 (1992), pp. 1384–1388; and Journal of Materials Science 28 (1993), pp. 2035–2039).

A disadvantage of such sensors is that the sensor effect does not become significant until a relatively high temperature (at least 500° C.), so that the requisite local equilibrium between $Na_2CO_3$ and the $Na^+$-ion-conducting solid electrolyte ceramic for adequate long-term stability no longer exists. The system is far from a state of chemical equilibrium. Carbonates such as $Na_2CO_3$, especially at elevated temperature, destructively attack the substances proposed thus far for the solid electrolyte ceramic, causing chemical disintegration, which severely shortens the service life and the time available for a stable display of valid measurement values.

SUMMARY OF THE INVENTION

It is accordingly an object of the invention to provide a $CO_2$ sensor and a measurement circuit using the sensor, which overcome the hereinafore-mentioned disadvantages of the heretofore-known devices of this general type, which have high long-term stability and which respond at a lower temperature, as low as room temperature.

With the foregoing and other objects in view there is provided, in accordance with the invention, a $CO_2$ sensor, comprising a body of solid electrolyte ceramic with alkali ion conductivity, and two electrodes of conductor material being inert with respect to the solid electrolyte ceramic, at least one of the electrodes being at least partially permeable, and the solid electrolyte ceramic being galvanically prepolarized.

In accordance with another feature of the invention, the solid electrolyte ceramic body and the partially permeable electrode are substantially flat.

In accordance with a further feature of the invention, there is provided a heater for heating the solid electrolyte ceramic body to a predetermined operating temperature.

In accordance with an added feature of the invention, the solid electrolyte ceramic is a compound of the NASICON structural type.

In accordance with an additional feature of the invention, there are provided transition metal cations of high redox potential being isomorphically incorporated into the NASICON solid electrolyte ceramic.

In accordance with yet another feature of the invention, the transition metal cations are iron cations.

In accordance with yet a further feature of the invention, there is provided a quantity of $Na_2CO_3$ formed in contact with air in the vicinity of the at least partially permeable electrode by galvanic polarization in the solid electrolyte body.

In accordance with yet an added feature of the invention, the conductor material of the electrodes is platinum.

With the objects of the invention in view there is also provided a measurement circuit configuration, comprising a $CO_2$ sensor including a body of solid electrolyte ceramic with alkali ion conductivity, and two electrodes of conductor material being inert with respect to the solid electrolyte ceramic, at least one of the electrodes being at least partially permeable, and the solid electrolyte ceramic being galvanically prepolarized; and a voltage measuring device coupled to the electrodes of the solid electrolyte ceramic body.

In accordance with another feature of the invention, the voltage measuring device is a device of high impedance as compared to an internal resistance of the solid electrolyte ceramic body.

In accordance with a concomitant feature of the invention, there is provided a periodically actuatable time switch coupling the voltage measuring device to the electrodes of the solid electrolyte ceramic body.

With a solid electrolyte ceramic body of high alkali ion conductivity as the point of departure, according to the invention the compound on which the ceramic is based proves to be stable relative to $Na_2CO_3$, for instance at 300° C., which is the operating temperature of the sensor, and the solid electrolyte ceramic body is provided with two electrodes of metal that is inert relative to the solid electrolyte ceramic, at least one of which is constructed to be generally flat and as at least partially permeable to $CO_2$.

Some other alkali metal, above all potassium or lithium, can be used instead of sodium in solid electrolyte ceramics. However, sodium exhibits the highest charge carrier mobility.

A noble metal, above all platinum, is recommended as the material for the electrodes. The separate use of a carbonate such as $Na_2CO_3$ in the electrode region of the solid electrolyte ceramic is intentionally rejected.

The essence of the invention is that an amount of $Na_2CO_3$ that is extremely slight for the $CO_2$ sensitivity is galvanically produced at the particle boundaries of the alkali-ion-conducting solid electrolyte ceramic in the region of the one partially permeable electrode through the use of an externally applied voltage or voltage pulse or a train of voltage pulses. As a result, the $CO_2$ sensor function is brought about and can be readjusted at any time, and the alkali-ion-conducting solid electrolyte ceramic, for instance of the NASICON type of composition $Na_{2+x}Fe^{III}_{1+x}Zr_{1-x}(PO_4)_3$, where $0<x<0.5$, or $Na_3Fe^{III}Sc(PO_4)_3$, which is used in the form of a tablet being a few millimeters in diameter and from 0.5 to 3 mm in thickness or in the form of a screen-printed layer on a substrate, such as $Al_2O_3$ ceramic, or in the form of a thin self-supporting sheet, proves to be stable at the operating temperature of the sensor relative to the slight quantity of $Na_2CO_3$ generated by galvanic polarization.

In addition, according to the invention, the generation of the $CO_2$ sensitivity is brought about by a specific solid-state electrochemical reaction, in such a way that transition metal cations are introduced by coupled isomorphic substitution into the NASICON structure. Due to their various oxidation stages in the process of galvanic polarization, these cations enable a defined anodic oxidation, as a result of which $Na^+$ ions, for instance corresponding to $2Na_3Fe^{III}Sc(PO_4)_3 <=> 2Na_2Fe^{IV}Sc(PO_4)_3 + 2Na^+ + 2$ e, are released, which migrate through the solid electrolyte ceramic to the cathode where, with electron acceptance from the partially permeable electrode and oxygen from the air and $CO_2$, in accordance with $2Na^+ + 2$ e $+ ½O_2 + CO_2 <=>$ form $Na_2CO_3$, sodium carbonate, in the intermediate particle range of the ceramic.

$Na^+$-ion-conducting solid electrolyte ceramics of the NASICON type having the CoII/CoIII redox pair, corresponding to the redox equilibrium $2Na_3Co^{II}Zr(PO_4)_3 <=> 2Na_2Co^{III}Zr(PO_4)_3 + 2Na^+ + 2$ e, or the MnII/MnIII redox pair corresponding to $Na_3Mn^{II}Zr(PO_4)_3 <=> Na_2Mn^{III}Zr(PO_4)_3 + 2Na^+ + 2$ e, in the process of the galvanic polarization, likewise enable a defined anodic oxidation, with the release of $Na^+$ ions for $Na_2CO_3$ formation in the region of the cathode. However, the compounds $Na_3Co^{II}Zr(PO_4)_3$ and $Na_3Mn^{II}Zr(PO_4)_3$ in the presence of the slight quantity of $Na_2CO_3$ at 300° C., which is the often-employed operating temperature of the sensor, undergo oxidative decomposition in air. In other words, because of the relatively low redox potential of $Co^{II}/Co^{III}$ or of $Mn^{II}/Mn^{III}$, the tendency of the NASICON electrolyte to decompose by reaction with $Na_2CO_3$ is enhanced, and long-term stability is not assured.

In a further feature of the invention, this disadvantage is overcome by introducing iron into the NASICON structure, dictated by the substantially higher redox potential FeIII/FeIV. The long-term stability of such a ceramic in the presence of $Na_2CO_3$ in air exists even at elevated temperature, such as 300° C.

The preparation of compounds of the NASICON type with $Fe^{III}$ cations, such as the series

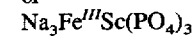, where $0<x<0.5$ or $Na_3Fe^{III}Sc(PO_4)_3$ is already known.

For instance, the compound $Na_3Fe^{III}Sc(PO_4)_3$ has already been described as a component of the mixed crystal series $Na_3Fe^{III}_{2x}Sc_{1-2x}(PO_4)_3$. The preparation is effected by way of the thermal composition of a mixture of $Sc_2O_3$, $Fe_2O_3$ with $NH_4H_2PO_4$ and $Na_2CO_3$ at 600° to 800° C. The preparation of compounds of the series 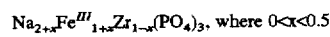 $(PO_4)_3$, such as $Na_2Fe^{III}Zr(PO_4)_3$ and $Na_{2.5}Fe^{III}_{1.5}Zr_{0.5}(PO_4)_3$ ($x=0$ and $0.5$, respectively) has so far also been done by way of the thermal conversion of a heterogeneous mixture of the corresponding starting materials.

Due to the incongruent melting of the compounds, which depending on the substance begins in the range from 1000° to 1100° C., the temperature usable for thermal synthesis of the pure single-phase compounds, is relatively limited at the top. It is therefore advantageous to perform the preparation by homogeneous precipitation out of the solution, which makes possible a molecularly dispersed particle distribution and an increased reactivity of the products of precipitation as compared with oxidic starting materials. In this way, homogeneous projects are more readily accessible. This kind of preparation includes the following steps:

selection and characterization of suitable water-soluble starting materials;

making up defined solutions;

converting these solutions;

inspissating the reaction mixture;

grinding the powdered mixture;

calcining the specimens to remove volatile components;

regrinding the presintered products;

compacting the powered products into tablets, using a compacting aid;

final sintering of these tablets.

Shaping of the alkali-ion-conducting solid electrolyte ceramic can also be carried out by making paste and using a sheet technique, followed by attaching the electrodes and sintering, or application in the layer sequence electrode/ceramic/electrode to a substrate, such as $Al_2O_3$, $SiO_2$ or Mullite, by a process of thick-film technology. The sensor property does not arrive until it arrives as a result of the polarization in the form of an EMF, based on very slight material changes in the region of the electrodes, and it fades in the form of a depolarization current during the function as a $CO_2$ sensor. Due to the long-term character of the electrochemical back reaction, the result is the development of a chronological plateau in the EMF.

Unlike static configurations of the prior art, this kind of dynamic sensor makes it unnecessary to line the solid electrolyte with an $Na_2CO_3$ layer. Ruinous destruction of the solid electrolyte does not occur. This is because upon application of the polarization voltage, an extremely slight quantity of $Na_2CO_3$ is formed in the region of the one partially permeable electrode at the particle limits, in such close contact with the alkali-ion-conducting solid electrolyte ceramic that reversible equilibrium adjustment is already possible at 300° C. and below, and a solid electrolyte ceramic being formed of $Na_3Fe^{III}Sc(PO_4)_3$ or a compound of the series $Na_{2+x}Fe^{III}_{1+x}Zr_{1-x}(PO_4)_3$, for instance $Na_2Fe^{III}Zr(PO_4)_3$, or $Na_{2.5}Fe^{III}_{1.5}Zr_{0.5}(PO_4)_3$, is used that proves to be stable with respect to the extremely slight amount of $Na_2CO_3$ under these conditions in air.

As discussed in more detail below, the galvanic prepolarization can be accomplished in air at 300° C. using low current, for example, between 0.1 and 1.0 mA over a period from 1 minute to 5 hours. The quantity of $Na_2CO_3$ produced in the vicinity of the permeable electrode is proportional to the charge transported by the galvanic prepolarization.

The EMF generated by polarization of the alkali-ion-conducting ceramic exhibits a temperature dependency that is within the framework of generally valid principles for galvanic cells, as expressed by Nernst's equation. When the $CO_2$ sensor is used under variable temperature conditions, a temperature-dependent correction of the display or of the measured values is therefore recommended, for instance by an associated microprocessor in combination with a temperature sensor, such as a thermistor or a platinum resistance element, in order to control the heating device that keeps the sensor at least at approximately constant temperature. The EMF generated by polarization can also be predetermined in this way through the use of certain desired values. Embodiments for establishing defined operation conditions are known in sensor technology. Information on them is found in the publication entitled "Applikations- und Schaltungsinformation 4" [Application and Circuit Information 4] (1988) by the firm UNITRONIC GmbH in Dusseldorf, Germany, regarding the FIGARO gas sensor TGS 203 for detecting CO, which is based on the change in conductivity of an oxide semiconductor.

Other features which are considered as characteristic for the invention are set forth in the appended claims.

Although the invention is illustrated and described herein as embodied in a $CO_2$ sensor and a measurement circuit using the sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a schematic and diagrammatic view of one embodiment of a sensor according to the invention showing reversible reactions in the case where $Na_2Fe^{III}Zr(PO_4)_3$ is used as a solid electrolyte ceramic;

FIG. 2 is a graph of behavior over time of EMF in volts as a function of time t in minutes of cylindrical sintering compacts made of $Na_2Fe^{III}Zr(PO_4)_3$;

FIG. 3 is a graph of time dependency of the EMF for an $Na_2Fe^{III}Zr(PO_4)_3$ ceramic.

DESCRIPTION OF THE PREFERRED EMBODIMENTS

Figure 4:
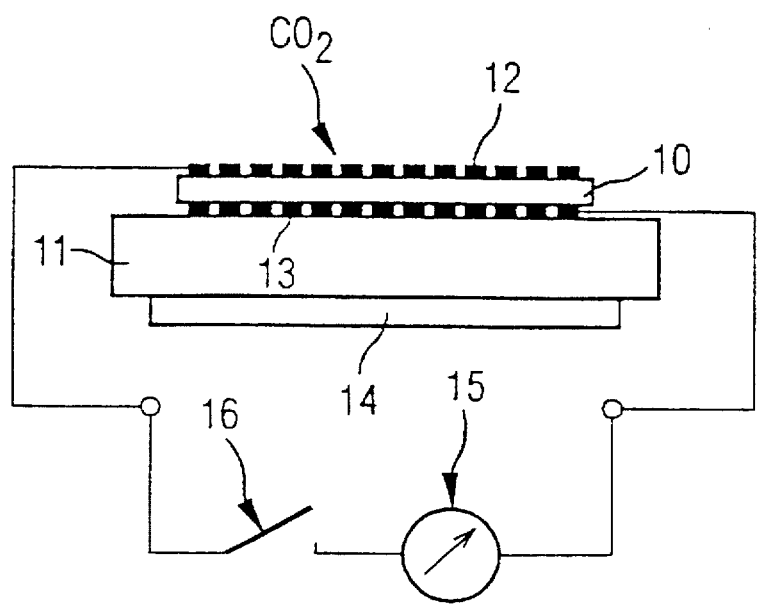
FIG. 4 is a schematic and diagrammatic view of one embodiment of a $CO_2$ sensor according to the invention.

Referring now to the figures of the drawings in detail and first, particularly, to FIG. 1 thereof, there is seen an example of a function course of a sensor according to the invention in the case where $Na_2Fe^{III}Zr(PO_4)_3$ is used as a solid electrolyte ceramic. A solid electrolyte ceramic body 1 is provided that has electrodes 2, 3 of platinum, of which at least one electrode 2 is partially permeable to $CO_2$. The solid electrolyte ceramic is polarized through the use of a voltage source 4. Upon depolarization, an EMF occurs at the electrodes 2, 3.

Production of the ceramic is carried out in such a way that $(NH_4)H_2PO_4$, $Na_2CO_3$, $F(NO_3)_3 \cdot 9H_2O$ are dissolved in a molar ratio of 3:1:1 in dilute $HNO_3$. When an equivalent amount zirconium acetyl acetonate is added to it drop by drop, the solution changes into a gellike state. A residue which is obtained by inspissation of the solution produces a powder by being heated in stages up to 850° C. and held for 5 hours at this temperature. The powder is converted into a ceramic with 80% of the theoretical density after being processed into the granulate and ensuing compacting by sintering at 1000° C. (for up to 40 hours). The contacting by application of the platinum electrodes 2, 3 is accomplished by painting with a platinum paste and firing it at 800° C. In the polarization, an anode reaction leads to the formation of a very slight quantity of $NaFe^{IV}Zr(PO_4)_3+Na^+$ ions, which migrate through the solid electrolyte ceramic body to the cathode. Their electrochemical discharge and reaction with air leads to the formation of $Na_2CO_3$ along the particle boundaries in the cathode region. In the depolarization, that is operation as a $CO_2$ sensor, the EMF dependent on the $CO_2$ partial pressure is equivalent to the spontaneous affinity of the reaction in the reverse direction.

Through the use of the electrochemical equilibrium that comes to be established at the partially permeable electrode 2, the $CO_2$ sensitivity is developed, after the termination of the polarization process, through the use of the then-present, very slight quantity of $Na_2CO_3$.

FIG. 2 shows the behavior over time of the EMF in volts as a function of the time t in minutes of cylindrical sintered compacts of $Na_2Fe^{III}Zr(PO_4)_3$ being contacted with a platinum paste and having a length L=0.5 cm and a diameter of 0.93 cm at 300° C. after the galvanostatic polarization in air, with a duration which is indicated in each case. The depolarization curves show a brief drop of from a few minutes to half an hour, which opens into a chronological plateau that is regained even after repeated short-circuiting. This expresses the long-term nature of the back reaction between the reaction products formed in the polarization. If the polarization time is one second and the voltage applied is approximately 8 V at room temperature, the discharge can be followed chronologically through a load resistor. The charge transported during the polarization is proportional to the quantity of $Na_2CO_3$ formed in the cathode region. The magnitude of the EMF values measured after the polarization current has been turned off depends initially on the transported charge quantity, but after a suitable duration of galvanostatic polarization it becomes a constant value. A polarization time of 5 hours at 1 mA or 20 hours at 0.1 mA produces approximately the same EMF.

FIG. 3 shows the EMF in volts as a function of the time t in minutes for an $Na_2Fe^{III}Zr(PO_4)_3$ ceramic which has been polarized for one hour at 300° C. at 0.1 mA. At the plateau of the polarization curve, the dependency of the EMF on the $CO_2$ partial pressure at 300 in alternation between $CO_2$ (100%) and air (0.03%) can be seen, which shows the sensor effect.

A measurement circuit configuration using a miniaturized version of a $CO_2$ sensor according to the invention is diagrammatically shown in FIG. 4. A $CO_2$ sensor element 10 of $Na_2Fe^{III}Zr(PO_4)_3$ ceramic is located on a heatable substrate 11. A first platinum electrode 13 is provided on the substrate 11 serving as a carrier. The solid electrolyte ceramic sensor element 10 is applied by thick-film technology onto the platinum electrode 13. A second electrode 12 is applied to the solid electrolyte ceramic 10 and is porous, or in other words it is constructed to be permeable to $CO_2$. A heater 14 is disposed on a side of the substrate 11 remote from the thick film 10 and, for instance, is in the form of a screen-printed platinum resistor layer provided in a meandering pattern. The sensor element 10 is coupled to a voltage measuring device 15 through a time switch 16. The time switch 16 is preferably actuatable periodically and the voltage determined by the voltage measuring device 15 between the electrodes 12 and 13 serves as a measure of the $CO_2$ content of the surrounding gas atmosphere.

We claim:

1. A $CO_2$ sensor, comprising:

a body of galvanically prepolarized solid electrolyte ceramic formed of electrolyte granulate particles with boundaries and having alkali ion conductivity, two electrodes of conductor material being inert to said solid electrolyte ceramic, at least one of said electrodes being at least partially permeable, and a quantity of alkali carbonate located at said boundaries of said particles of said electrolyte ceramic in the vicinity of said at least partially permeable electrode, said electrolyte ceramic having a NASICON-type structure in which transition metal ions selected from the group consisting of cobalt, manganese and iron have been isomorphically integrated, and said sensor having no separate layer or cohesive body of alkali carbonate.

2. The $CO_2$ sensor according to claim 1, wherein said solid electrolyte ceramic body and said partially permeable electrode are substantially flat.

3. The $CO_2$ sensor according to claim 2, including a heater for heating said solid electrolyte ceramic body to a predetermined operating temperature.

4. The $CO_2$ sensor according to claim 1, wherein said transition metal cations are iron cations.

5. The $CO_2$ sensor according to claim 1, wherein said conductor material of said electrodes is platinum.

6. A measurement circuit configuration, comprising:

a $CO_2$ sensor including a body of galvanically prepolarized solid electrolyte ceramic formed of electrolyte granulate particles with boundaries and having alkali ion conductivity, two electrodes of conductor material being inert to said solid electrolyte ceramic, at least one of said electrodes being at least partially permeable, and a quantity of alkali carbonate located at said boundaries of said particles of said electrolyte ceramic in the vicinity of said at least partially permeable electrode, said electrolyte ceramic having a NASICON-type structure in which transition metal ion selected from the group consisting of cobalt, manganese and iron have been isomorphically integrated, and said sensor having no separate layer or cohesive body of alkali carbonate; and a voltage measuring device coupled to said electrodes.

7. The measurement circuit configuration according to claim 6, wherein said voltage measuring device is a device of high impedance as compared to an internal resistance of said solid electrolyte ceramic body.

8. The measurement circuit configuration according to claim 7, including a periodically actuatable time switch coupling said voltage measuring device to said electrodes.

* * * * *